(12) United States Patent
Jörgensen

(10) Patent No.: US 8,133,440 B2
(45) Date of Patent: *Mar. 13, 2012

(54) AROMATIC NEBULIZING DIFFUSER

(75) Inventor: Carsten Jörgensen, Kastanienbaum (CH)

(73) Assignee: Ming Jen Hsiao, Miaoli County (TW)

( * ) Notice: Subject to any disclaimer, the term of this patent is extended or adjusted under 35 U.S.C. 154(b) by 315 days.

This patent is subject to a terminal disclaimer.

(21) Appl. No.: 12/480,955

(22) Filed: Jun. 9, 2009

(65) Prior Publication Data

US 2010/0308129 A1 Dec. 9, 2010

(51) Int. Cl.
*A62B 7/08* (2006.01)
*A61L 9/04* (2006.01)
(52) U.S. Cl. .......................... 422/123; 239/34
(58) Field of Classification Search .................. 422/123; 239/34
See application file for complete search history.

(56) References Cited

U.S. PATENT DOCUMENTS 7,467,786 B2 * 12/2008 Jae-Bong et al. ............... 261/81

* cited by examiner

*Primary Examiner* — Kevin Joyner
(74) *Attorney, Agent, or Firm* — Ming Chow; Sinorica, LLC

(57) ABSTRACT

An aromatic nebulizing diffuser includes a base panel, a lower housing, power adapter, an electric fan, a speaker, a music control circuit, an ultrasonic oscillator carrying a light source, a fluid container, a waster shutter and a transmissive cover. When electrically connected, the ultrasonic oscillator is started to generate high frequency sound waves and to cause atomization of the aromatic fluid contained in the fluid container so that a mist of aerodynamic breakup of fine water drops is seen through the transmissive cover and at the same time, the music control circuit outputs a music through the speaker and the light source emits a mixed color of light to light up the mist of aerodynamic breakup of fine water drops that is forced out of the hole on the top side of the transmissive cover.

14 Claims, 6 Drawing Sheets

AROMATIC NEBULIZING DIFFUSER

BACKGROUND OF THE INVENTION

1. Field of the Invention

Figure 1:
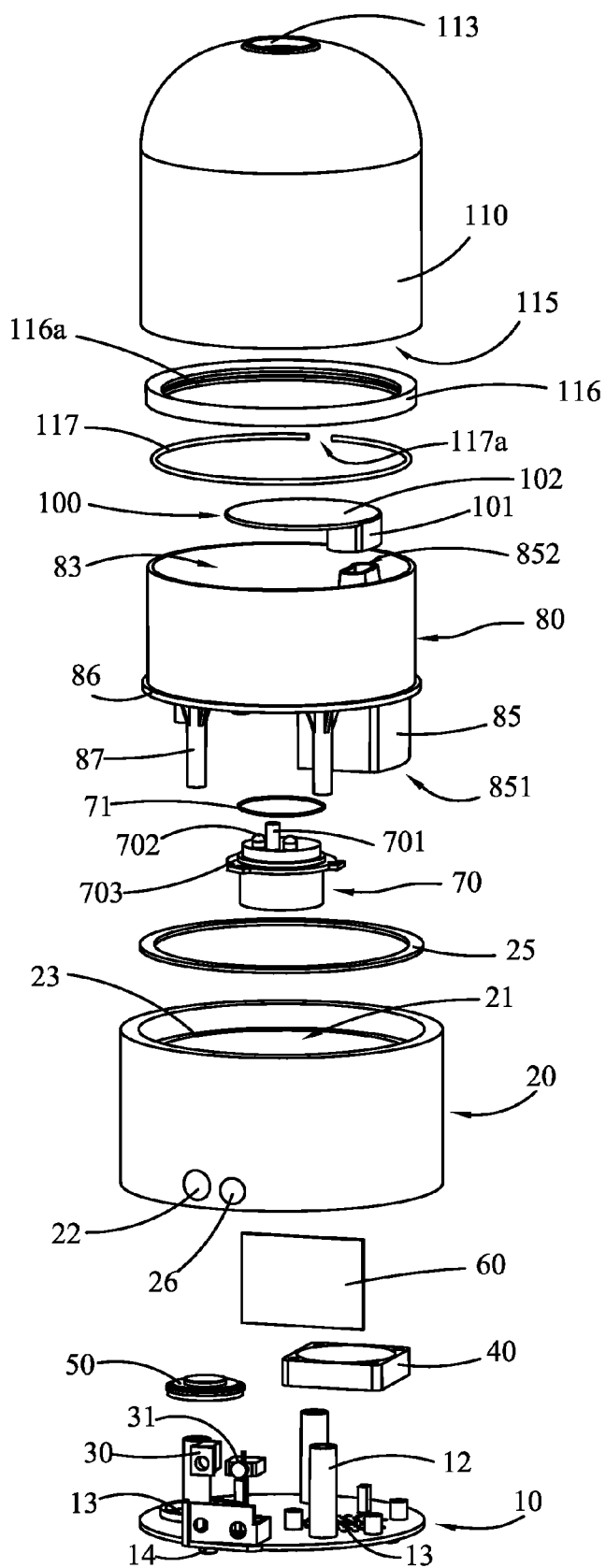
Figure 2:
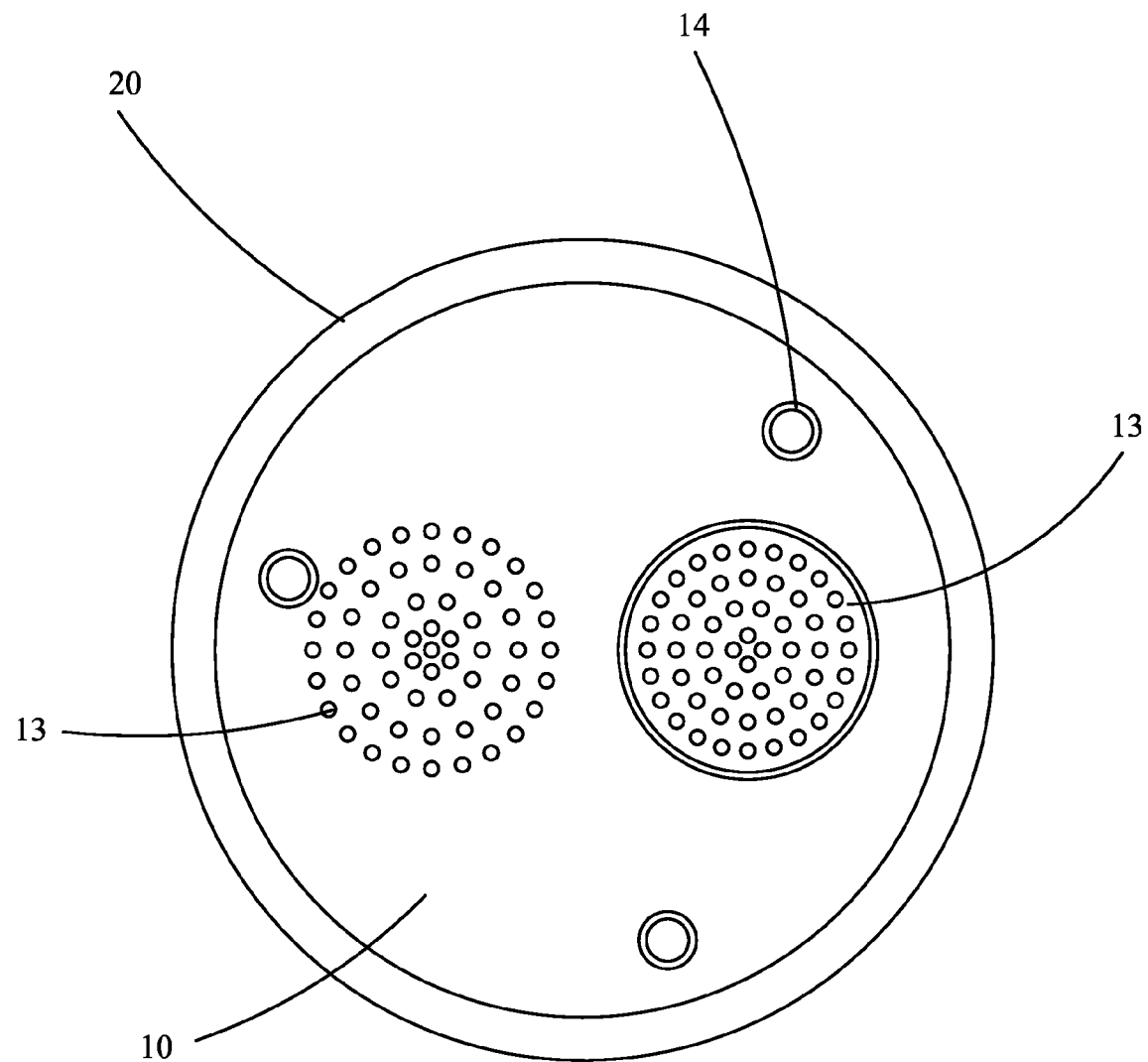
Figure 3:
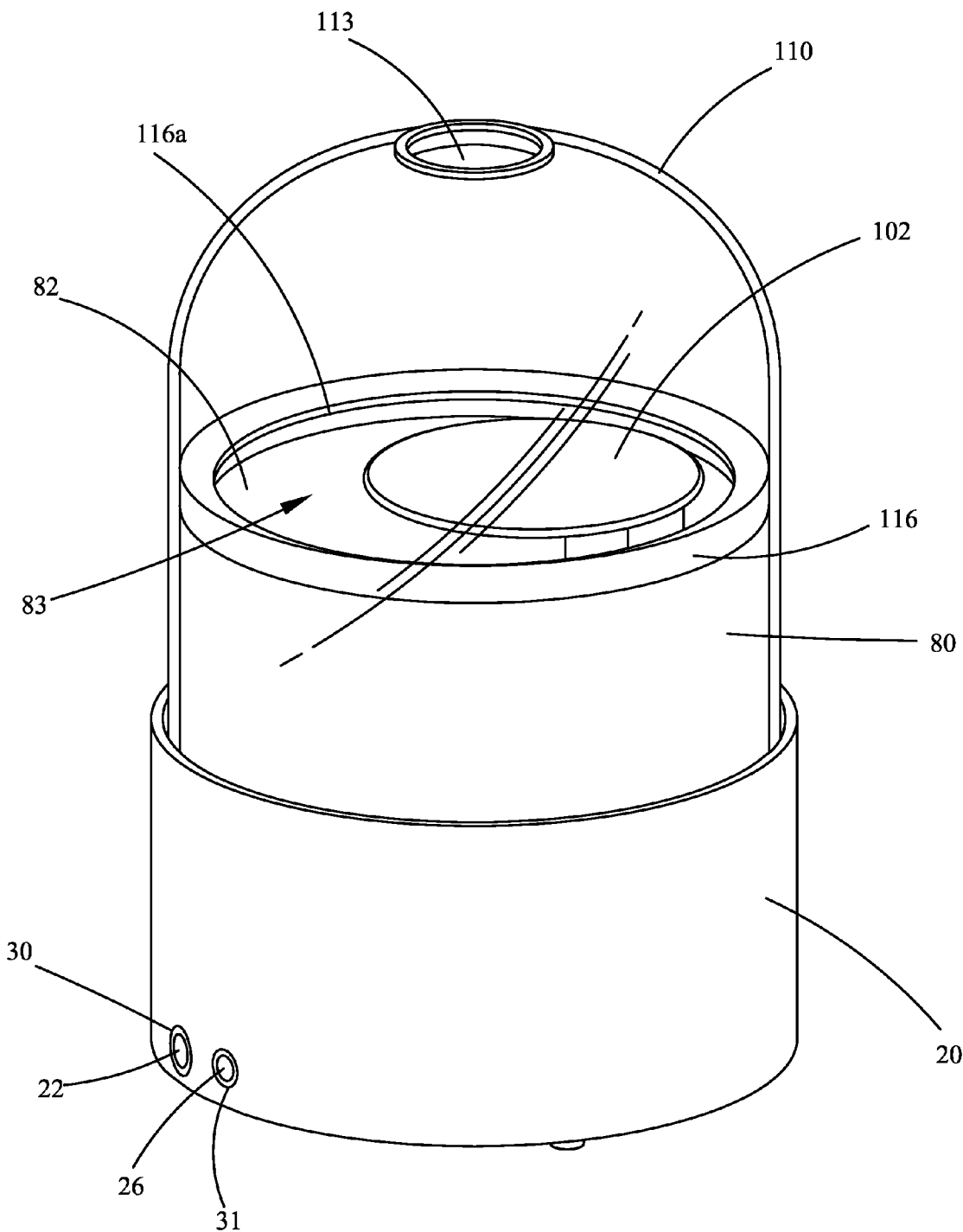
Figure 4:
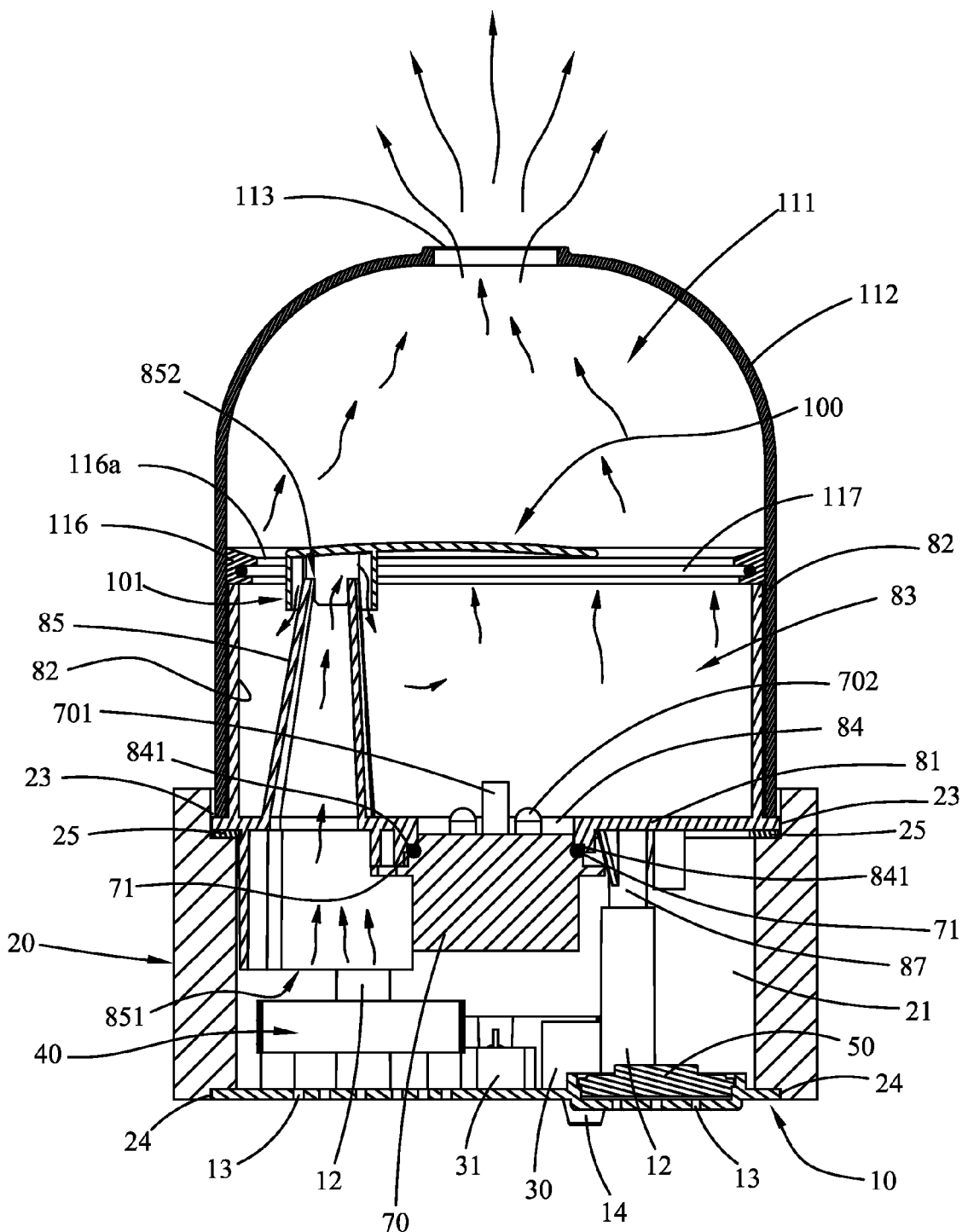
Figure 5:
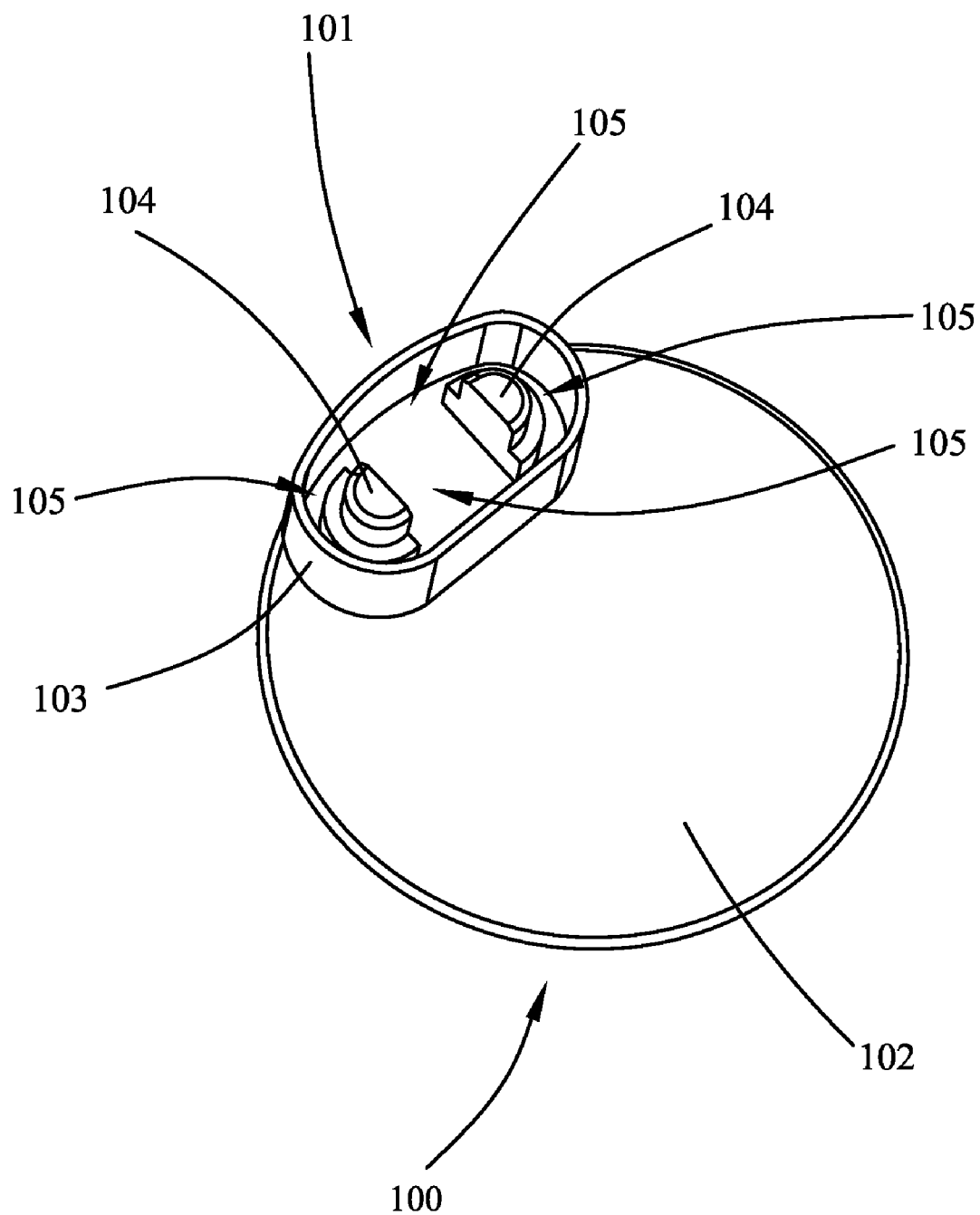
Figure 6:
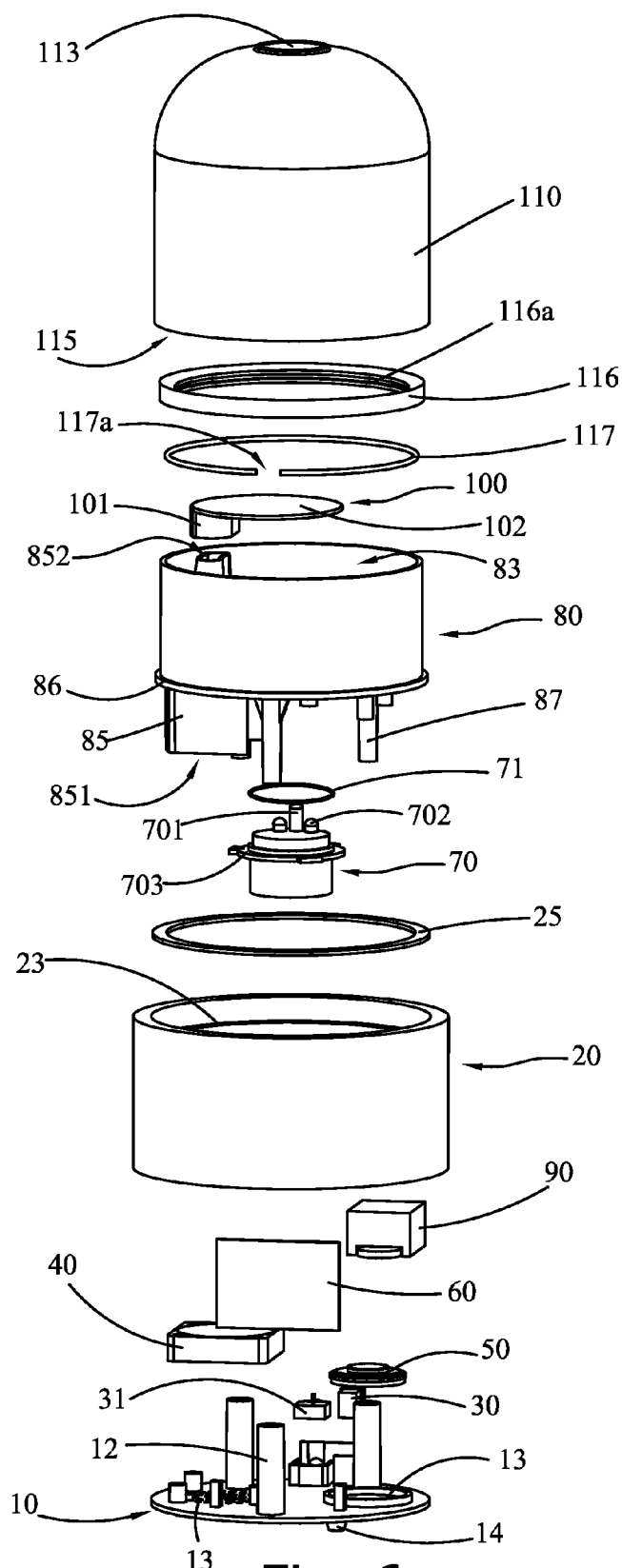

The present invention relates to an aromatic nebulizing diffuser and more particularly, to such a nebulizing diffuser that provides sound, lighting and visual effects.

2. Description of the Related Art

A known essential oil diffuser uses an ultrasonic oscillator to generate a high ultrasonic energy facilitating atomization of an essential oil for application. Separation of electric charges in falling rain, caused by breaking up of the water droplets, the drops becoming positively charged and the air negatively charged. This separation of electric charges accompanying the aerodynamic breakup of water drops is known as spray electrification, the waterfall effect or Lenard effect. Conventional aromatic nebulizing diffusers simply produce an upwardly flying mist of aromatic gas. They cannot simulate the natural visual effect of a flying mist caused by the impact of a waterfall.

A known aromatic nebulizing diffuser utilizes a vibrator to vibrate a mixture of essential oil and water in producing a mist of fine drops of the mixture of essential oil and water. After a certain period of use, the inside of the diffuser will be contaminated with essential oil stains. In this case, the diffuser must be cleaned so as not to lower the nebulizing performance. However, it is inconvenient to assemble and disassemble the diffuser, i.e., the cleaning work of this design of aromatic nebulizing diffuser is complicated.

There is known another structure of aromatic nebulizing diffuser that utilizes an ultrasonic oscillator to oscillate an aromatic fluid in producing a mist of fine drops of aromatic fluid. During oscillation of the ultrasonic oscillator, the aromatic fluid may leaks into the lower part of the diffuser to wet the internal electronic components and other mechanism, causing damage or lowering the performance.

There is known still another design of aromatic nebulizing diffuser in which stirring of excessive fluid above the oscillator interferes with formation of mist, lowering the generation of mist.

There are known some other aromatic nebulizing diffusers which provide a lighting effect. However, the lighting effect is not attractive in daylight. Further, the non-transmissive housing does not facilitate viewing of a mist accompanying with a colorful change of light.

Further, conventional aromatic nebulizing diffusers commonly have a limited internal space and a small flow passage that guides a forced flow of air to induce a mist, in consequence, the amount of flying mist is limited. Therefore, an improvement on the flow passage to facilitate the formation of a mist is expected.

In recent years, tourist hotel industry introduces an aromatic soothing air environment by means of utilizing the air conditioning system to spread an aromatic gas into the air. However, the engineering of this design is complicated and requires a big amount of investment, not suitable for ordinary consumers.

There is known still another aromatic nebulizing diffuser, which utilizes pressure means to force an essential oil and water mixture into a thin line of water-column in an internal cavity, for enabling the thin line of water-column to be diffused into a mist and ejected out of the top side of the internal cavity. This design rapidly diffuses a mist of essential oil and water mixture, however this design of aromatic nebulizing diffuser is less precision and consumes essential oil rapidly, and therefore it is not widely accepted by consumers

SUMMARY OF THE INVENTION

The present invention has been accomplished under the circumstances in view. It is main object of the present invention to provide an aromatic nebulizing diffuser, which drives an ultrasonic oscillator to generate high frequency sound waves and to cause atomization of an aromatic fluid so that a mist of aerodynamic breakup of fine water drops is seen through a transmissive cover and at the same time, a music control circuit outputs a music through the speaker and a light source emits a mixed color of light to light up the mist of aerodynamic breakup of fine water drops that is forced out of a hole on the top side of a transmissive cover.

To achieve this and other objects of the present invention, an aromatic nebulizing diffuser comprises a base panel having air holes, an electric fan mounted on the base panel corresponding a part of the air holes, an ultrasonic oscillator having a control circuit therein and carrying a water level sensor and a light source, a power adapter electrically connected to the electric fan and the ultrasonic oscillator, a lower housing affixed to the bottom panel and defining an accommodation chamber that accommodates the power adapter, the electric fan and the ultrasonic oscillator, a fluid container, which has a bottom wall with a center opening for holding the ultrasonic oscillator, an upright peripheral wall joined to the border of the bottom wall and defining with the upright peripheral wall a fluid chamber, a pressure-charging airway vertically mounted therein and a flange extended from the bottom wall of the fluid container around the upright peripheral wall, the pressure-charging airway having a gas intake port extending through the bottom wall of the fluid container and vertically aimed at the electric fan, a gas exhaust port suspending in the fluid chamber and an inner diameter gradually reducing from the gas intake port toward the gas exhaust port, a water shutter, which has a pipe connector and a tongue plate, the pipe connector having a peripheral wall and two retaining rods surrounded by the peripheral wall and tightly fitted into the gas exhaust port of the pressure-charging airway and defining with peripheral wall at least one back-ejection puff port, and a transmissive cover, which has an open end capped on the fluid container and stopped between the flange of the fluid container and a part of the lower housing.

The transmissive cover of the aromatic nebulizing diffuser is shaped like a classic lantern that holds a mist of aerodynamic breakup of fine water drops during operation of the ultrasonic oscillator. Further, a negative ion generator is provided to generate negative ions when a mist of aerodynamic breakup of fine water drops is produced in the transmissive cover and the music control circuit is outputting a music through the speaker and the light source is emitting a mixed color of light to light up the mist of aerodynamic breakup of fine water drops, thereby offering a very delightfully warm and romantic atmosphere.

Further, the transmissive cover and the water shutter can be quickly mounted or dismounted without tools, facilitating cleaning.

Further, when an excessive amount of the mist of aerodynamic breakup of fine water drops is produced, condensed fluid flows along the top side of the ultrasonic oscillator to the inside of the fluid container, and the fluid is well sealed and prohibited from leaking into the inside of the lower housing to damage the internal electronic component parts.

Further, the invention eliminates the use of a specific essential bottle to contain an essential oil or any aromatic fluid. An aromatic fluid can be directly filled through the hole on the top side of the transmissive cover into the inside of the fluid chamber in the fluid container. Through the transmissive cover, the amount of the aromatic fluid contained in the fluid container can be checked visually.

Further, the design of the airway causes the pressure of currents of air being transferred by the electric fan into the fluid container to be increased. When the currents of air flow out of the airway, they are baffled by the pipe connector of the water shutter and forced to eject downwards out of the back-ejection puff port into the inside of the fluid chamber of the fluid container, causing the aromatic fluid to fly in drops and forcing the produced aerodynamic breakup of fine water drops to flow out of the hole of the transmissive cover rapidly. Therefore, the invention eliminates the drawback of the prior art designs of diffusing an essential oil in a slow motion where diffused fine drops tend to be gathered together and condensed, lowering the formation of a mist.

Further, the aromatic fluid to be filled in the fluid container can be fragrant fluid, water, essential oil, perfume, natural plant and flower extract fluids or their combinations.

Further, the transmissive cover can be made of a transparent or semi-transparent material, such as glass, frosted glass, acrylic, plastics or ceramic in a color design.

BRIEF DESCRIPTION OF THE DRAWINGS

FIG. 1 is an exploded view of an aromatic nebulizing diffuser in accordance with a first embodiment of the present invention.

FIG. 2 is a schematic bottom view of the aromatic nebulizing diffuser in accordance with the first embodiment of the present invention.

FIG. 3 is a perspective view of the aromatic nebulizing diffuser in accordance with the first embodiment of the present invention.

FIG. 4 is a schematic sectional view of the aromatic nebulizing diffuser in accordance with the first embodiment of the present invention.

FIG. 5 is an oblique bottom elevation of the water shutter of the aromatic nebulizing diffuser in accordance with the first embodiment of the present invention.

FIG. 6 is an exploded view of an aromatic nebulizing diffuser in accordance with a second embodiment of the present invention, showing a negative ion generator used therein.

DETAILED DESCRIPTION OF THE PREFERRED EMBODIMENT

Referring to FIGS. 1, 2 and 3, an aromatic nebulizing diffuser in accordance with a first embodiment of the present invention is shown comprising a base panel 10 having a plurality of air holes 13, an electric fan 40 mounted on the base panel 10 above a part of the air holes 13, an ultrasonic oscillator 70, which has a water level sensor 401 and a light source 702 mounted on the top side thereof and electrically connected to the internal control circuit (not shown) thereof, a power adapter 30 electrically connected to the electric fan 40 and the ultrasonic oscillator 70, a lower housing 20, which surrounds the top side of the base panel 10 and defines therein an accommodation chamber 21 that accommodates the power adapter 30, the electric fan 40 and the ultrasonic oscillator 70, and a fluid container 80, which has a bottom wall 81, an upright peripheral wall 82 joined to the border of the bottom wall 81 and defining with the upright peripheral wall 82 a fluid chamber 83. The fluid container 80 can be made of a transparent or semi-transparent material.

Referring also to FIG. 4, the fluid container 80 has a pressure-charging airway 85 vertically mounted therein. The pressure-charging airway 85 has a gas intake port 851 at its one end and a gas exhaust port 852 at its opposite end. The pressure-charging airway 85 has a diameter gradually reducing from the gas intake port 851 toward the gas exhaust port 852. The gas exhaust port 852 suspends in the fluid chamber 83. The gas intake port 851 extends through the bottom wall 81 and vertically aimed at the electric fan 40. The bottom wall 81 has a center opening 84 located on the center for the mounting of the ultrasonic oscillator 70. The fluid container 80 further has a flange 86 extended from the bottom wall 81 around the upright peripheral wall 82.

Referring to FIG. 5, the aromatic nebulizing diffuser further comprises a water shutter 100 and a transmissive cover 110. The water shutter 100 comprises a pipe connector 101 and a tongue plate 102. The pipe connector 101 has a peripheral wall 103 and two retaining rods 104 surrounded by the peripheral wall 103. The two retaining rods 104 and the peripheral wall 103 define at least one back-ejection puff port 105. The two retaining rods 104 are tightly fitted into the gas exhaust port 852 so that the tongue plate 102 extends radially to shield the ultrasonic oscillator 70 and the fluid filled in the fluid chamber 83. The transmissive cover 110 has an open end 115 disposed at one end, and a hole 113 disposed at the other side opposite to the open end 115. By means of the open end 115, the transmissive cover 110 is capped on the fluid container 80. When the transmissive cover 110 is capped on the fluid container 80, the open end 115 is stopped between the flange 86 of the fluid container 80 and a part of the lower housing 20. Thus, mounting and dismounting of the transmissive cover 110 and the water shutter 120 are easy without tools, facilitating cleaning.

Based on the aforesaid arrangement, the user needs not to open the cover and then to put an essence bottle in the aromatic nebulizing diffuser like the prior art design. The invention allows aromatic substances (essential oil) and water to be directly filled through the hole 113 into the fluid chamber 83 in the water container 80.

Referring to FIGS. 1, 3 and 4 again, the transmissive cover 110 has a rubber water seal ring 116 and a tension ring 117 mounted therein. The rubber water seal ring 116 defines therein an annular inside locating groove 116*a*. The tension ring 117 is a C-shaped ring having an opening 117*a* and a diameter greater than the annular inside locating groove 116*a*. Thus, by means of compression the opening 117*a* to shorten the diameter of the tension ring 117, the tension ring 117 can be put in the annular inside locating groove 116*a*. After installation of the tension ring 117 in the annular inside locating groove 116*a*, the tension ring 117 releases tension to support the rubber water seal ring 116 in shape, forcing the rubber water seal ring 116 in close contact with the inside wall of the transmissive cover 110 to avoid fluid leakage, which may affect the performance of or damage the electronic component parts in the lower part of the aromatic nebulizing diffuser, due to stirring of the fluid by the oscillation of the ultrasonic oscillator 70 or deterioration damage of the rubber water seal ring 116 caused by the machine or external environment. Therefore, the waterproof effect of the aromatic nebulizing diffuser is superior to conventional designs.

Thus, when electrically connected, aromatic fluid is filled through the hole 113 into the fluid chamber 83 in the water container 80, and the ultrasonic oscillator 70 is started to generate high frequency sound waves. At this time, atomization of the aromatic fluid is produced, and a mist of aerodynamic breakup of fine water drops in the inside space 111 of the transmissive cover 110 is seen through the transmissive cover 110. At the same time, the light source 702 emits light to light up the mist of aerodynamic breakup of fine water drops that is forced out of the hole 113 of the transmissive cover 110.

Further, the ultrasonic oscillator 70 has an outside annular flange 703 extending around the periphery, and a water seal ring 71 mounted on the outside annular flange 703. The bottom wall 81 of the fluid container 80 has an inside annular groove 841 formed in the center opening 84. After installation of the ultrasonic oscillator 70 in the center opening 84, the water seal ring 71 is engaged into the inside annular groove 841 to seal the gap, avoiding fluid leakage.

The ultrasonic oscillator 70 oscillates at a frequency over several hundred thousands of times or several million times per second to oscillate the aromatic fluid, causing an oscillating water column to be produced and ejected upwards. At this time, the circular tongue plate 102 of the water shutter 100 depresses the upwardly ejecting oscillating water column, thus a big amount of aerodynamic breakup of water drops is produced to fill up the inside space 111 of the transmissive cover 110. The electric fan 40 transfers currents of air to the gas intake port 851 of the pressure-charging airway 85 toward the gas exhaust port 852. Because the airway 85 has a diameter gradually reducing from the gas intake port 851 toward the gas exhaust port 852, the flow of air is concentrated and the pressure of the flow of air is increased. When the concentrated flow of air flows out of the airway 85, it is baffled by the pipe connector 101 of the water shutter 100 and forced to eject downwards out of the back-ejection puff port 105 into the inside of the fluid chamber 83 of the fluid container 80, causing the aromatic fluid to fly in drops and forcing the produced aerodynamic breakup of fine water drops to flow out of the hole 113 rapidly.

Further, the light source 702 at the top side of the ultrasonic oscillator 70 is preferably a LED light comprising a red LED chip, a blue LED chip and a green LED chip, or a multi-color LED chip that emits red, blue and green light. By means of the control of the internal control circuit of the ultrasonic oscillator 70, the light source 702 emits a mixed light of multiple colors to light up the transmissive cover 119 and the internal aromatic fluid and mist of fine drops of aromatic fluid. At the same time, the internal control circuit of the ultrasonic oscillator 70 controls flashing and color change of the light source 702 subject to the rhythm of an audio signal received from a music control circuit 60, creating fantastic visual, sound and lighting effects.

The aforesaid lower housing 20 comprises a water seal ring 25, an upper inside annular groove 23, a lower inside annular groove 24 and a power hole 22 corresponding to the power adapter 30. The water seal ring 25 is squeezed in between the flange 86 of the fluid container 80 and the upper inside annular groove 23 of the aforesaid lower housing 20. The aforesaid base panel 10 is press-fitted into the lower inside annular groove 24 of the lower housing 20. The lower housing 20 can be made of ceramics, wood, glass, plastics or glass fibers. The base panel 10 has a plurality of hollow columns 12. The fluid container 80 has a plurality of bottom mounting rods 87 respectively plugged into the hollow columns 12 and fixedly secured thereto with screws (not shown).

Referring to FIGS. 1~3 again, the aromatic nebulizing diffuser further comprises a speaker 50 mounted on the base panel 10 over a part of the air holes 13 and the aforesaid music control circuit 60 that provides an audio signal for output through the speaker 50 to produce a sound effect in accompany with the aforesaid visual and lighting effects.

The music control circuit 60 has storage means for the storage of natural sound, music, human voices, animal calls, bird's song and water and sound of running water subject to personal's preference to join with the aforesaid visual and lighting effects, creating a personal initiative environment.

Referring also to FIG. 5, the aromatic nebulizing diffuser further comprises an audio input connector 31. The audio input device 31 is fixedly mounted on the base panel 10 to receive audio signal from an external music player or system. The lower housing 20 further has a connector hole 26 corresponding to the audio input connector 31. The audio input connector 31 can be a USB jack, music player connector, palmtop electronic music player connector, or telephone jack.

FIG. 6 illustrates an aromatic nebulizing diffuser in accordance with a second embodiment of the present invention. This second embodiment has a negative ion generator 90 mounted on the base panel 10 and electrically connected to the power adapter 30 for generating negative ions.

The base panel 10 according to this second embodiment has a plurality of foot members 14 for supporting the aromatic nebulizing diffuser on a tabletop or the floor to keep the air holes 13 apart from the tabletop or floor at a distance so that outside currents of air can be drawn through the air holes 13 into the inside of the aromatic nebulizing diffuser and sound waves can be driven out of the aromatic nebulizing diffuser through the air holes 13 smoothly. Keeping the air holes 13 apart from the tabletop or floor at a distance also facilitates dissipation of heat.

Further, the aforesaid water level sensor 701 is disposed slightly above the elevation of the bottom wall 81 of the fluid container 80. When the level of the aromatic fluid in the fluid container 80 dropped below the elevation of the top side of the water level sensor 701, the water level sensor 701 immediately gives a signal to the internal control circuit of the ultrasonic oscillator 70 to cut off power supply from the ultrasonic oscillator 70, avoiding damage.

When compared to the prior art designs that simple enables people to enjoy a pleasant smell, the aromatic nebulizing diffuser enables people to view a mist in the transmissive cover 110 while generating a pleasant smell and negative ions and producing fantastic visual, sound and lighting effects. Therefore, the invention offers people a very delightfully warm and romantic atmosphere.

A prototype of aromatic nebulizing diffuser has been constructed with the features of FIGS. 1~6. The aromatic nebulizing diffuser functions smoothly to provide all of the features disclosed earlier.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. An aromatic nebulizing diffuser, comprising:

a base panel, said base panel having air holes cut through top and bottom sides thereof;

an electric fan mounted on said base panel corresponding a part of said air holes;

an ultrasonic oscillator having a control circuit therein, said ultrasonic oscillator carrying a water level sensor and a light source on a top side thereof, said water level sensor and said light source being electrically connected to the control circuit of said ultrasonic oscillator;

a power adapter electrically connected to said electric fan and said ultrasonic oscillator;

a lower housing affixed to said bottom panel and defining an accommodation chamber that accommodates said power adapter, said electric fan and said ultrasonic oscillator;

a fluid container holding a fluid, said fluid container having a bottom wall, an upright peripheral wall joined to the border of said bottom wall and defining with the upright peripheral wall a fluid chamber, a pressure-charging airway vertically mounted therein and a flange extended from the bottom wall of said fluid container around said upright peripheral wall, said pressure-charging airway having a gas intake port at one end thereof and a gas exhaust port at an opposite end thereof, said pressure-charging airway having a diameter gradually reducing from said gas intake port toward said gas exhaust port, said gas exhaust port suspending in said fluid chamber, said gas intake port extending through the bottom wall of said fluid container and vertically aimed at said electric fan, the bottom wall of said fluid container having a center opening that holds said ultrasonic oscillator;

a water shutter, said water shutter comprising a pipe connector and a tongue plate, said pipe connector having a peripheral wall and two retaining rods surrounded by the peripheral wall, the two retaining rods and peripheral wall of said pipe connector defining at least one back-ejection puff port, said two retaining rods being tightly fitted into said gas exhaust port of said pressure-charging airway so that said tongue plate extends radially to shield said ultrasonic oscillator and the fluid contained in said fluid chamber; and a transmissive cover capped on said fluid container, said transmissive cover having an open end and a hole opposite to said open end, said open end being stopped between the flange of said fluid container and a part of said lower housing.

2. The aromatic nebulizing diffuser as claimed in claim 1, further comprising a music control circuit electrically connected to said ultrasonic oscillator such that the control circuit of said ultrasonic oscillator receives an audio signal from said music control circuit and controls flashing and light emitting of said light source subject to the rhythm of the audio signal received from said music control circuit, said music control circuit having storage means for the storage of natural sound, music, human voices, animal calls, bird's song and water and sound of running water.

3. The aromatic nebulizing diffuser as claimed in claim 1, wherein said transmissive cover has a rubber water seal ring and a tension ring mounted therein, said rubber water seal ring defining therein an annular inside locating groove, said tension ring being a C-shaped ring having an opening and a diameter greater than said annular inside locating groove of said rubber water seal ring, said tension ring being set in the annular inside locating groove of said rubber water seal ring to support said rubber water seal ring in close contact with and inside wall of said transmissive cover.

4. The aromatic nebulizing diffuser as claimed in claim 1, wherein the bottom wall of said fluid container has an inside annular groove formed in the center opening thereof; said ultrasonic oscillator has an outside annular flange extending around the periphery thereof and a water seal ring mounted on the outside annular flange and engaged into the inside annular groove in the center opening of the bottom wall of said fluid container.

5. The aromatic nebulizing diffuser as claimed in claim 1, wherein said lower housing comprises an upper inside annular groove, a water seal ring squeezed in between the flange of said fluid container and the upper inside annular groove of said lower housing, a lower inside annular groove, which receives said base panel.

6. The aromatic nebulizing diffuser as claimed in claim 1, wherein said lower housing is selected from a material group of ceramics, wood, glass, plastics and glass fibers.

7. The aromatic nebulizing diffuser as claimed in claim 1, wherein said fluid contained in said fluid container is selected from the group of fragrant fluid, water, essential oil, perfume, natural plant and flower extract fluids and their combinations.

8. The aromatic nebulizing diffuser as claimed in claim 1, wherein said base panel has a plurality of hollow columns; said fluid container has a plurality of bottom mounting rods respectively plugged into said hollow columns of said base panel and fixedly secured thereto with screws.

9. The aromatic nebulizing diffuser as claimed in claim 1, further comprising a speaker mounted on said base panel over a part of said air holes and a music control circuit electrically connected to said speaker and adapted to provide an audio signal for output through said speaker.

10. The aromatic nebulizing diffuser as claimed in claim 1, wherein said fluid container is selectively prepared from a transparent or semi-transparent material.

11. The aromatic nebulizing diffuser as claimed in claim 1, further comprising audio input connector adapted to receive an audio signal from an external signal source.

12. The aromatic nebulizing diffuser as claimed in claim 1, further comprising a negative ion generator.

13. The aromatic nebulizing diffuser as claimed in claim 1, wherein said light source is a LED (light emitting diode) light source.

14. The aromatic nebulizing diffuser as claimed in claim 13, wherein said light source is controllable by the control circuit of said ultrasonic oscillator to emit red light, blue light and green light.

* * * * *